United States Patent
Breker et al.

(10) Patent No.: US 6,517,819 B1
(45) Date of Patent: Feb. 11, 2003

(54) ANTIPERSPIRANT SUSPENSIONS CONTAINING FINELY DIVIDED ALUMINIUM AND ZIRCONIUM, HAVING BETTER EFFECTIVENESS AND A PROCESS FOR THEIR MANUFACTURE

(75) Inventors: Johannes Breker, Ludwigshafen (DE); Bruno Kaufmann, Frankenthal (DE); Wolfgang Reibel, Ludwigshafen (DE); Klaus Schanz, Dannstadt (DE)

(73) Assignee: BK Giulini Chemie GmbH und Co Ohg, Ludwigshafen (DE)

( * ) Notice: Subject to any disclaimer, the term of this patent is extended or adjusted under 35 U.S.C. 154(b) by 0 days.

(21) Appl. No.: 09/579,506

(22) Filed: May 26, 2000

(30) Foreign Application Priority Data

May 29, 1999 (EP) .............................. 99110455

(51) Int. Cl.⁷ ............................ A61K 7/32; A61K 7/34; A61K 7/38; A61K 33/06
(52) U.S. Cl. ............................ 424/65; 424/66; 424/68; 424/401; 424/682; 424/685
(58) Field of Search ............................ 424/401, 65, 66, 424/68, 682, 685

(56) References Cited

U.S. PATENT DOCUMENTS

| | | | | |
|---|---|---|---|---|
| 5,444,096 A | * | 8/1995 | McCrea et al. ............. 514/770 |
| 5,723,135 A | * | 3/1998 | Ford et al. ................... 424/401 |
| 5,955,065 A | * | 9/1999 | Thong et al. ................. 424/68 |
| 5,969,172 A | * | 10/1999 | Nye ............................ 556/445 |
| 6,136,302 A | * | 10/2000 | Juneja et al. ................. 424/65 |
| 6,231,259 B1 | * | 5/2001 | Murgida et al. ............. 401/175 |

FOREIGN PATENT DOCUMENTS

GB 2 144 992 A * 3/1985

* cited by examiner

Primary Examiner—Jose' G. Dees
Assistant Examiner—Marina Lamm
(74) Attorney, Agent, or Firm—Venable; George H. Spencer; Ashley J. Wells

(57) ABSTRACT

An antiperspirant suspension which is finely divided, which is contained in a non-aqueous phase, and which has improved efficacy for perspiration reduction when used on human skin, includes at least one basic aluminum-zirconium-halogenohydrate complex as active ingredient in which at least 60% of the zirconium content can be directly titrated after dissolving in 0.1 n HCl with EDTA at a pH of 0.8, wherein the active ingredient optionally contains an amino acid. A process for the synthesis of the antiperspirant suspension includes mixing an aluminum salt which is effective as an antiperspirant with a zirconium salt which is effective as an antiperspirant, optionally in the presence of an amino acid, in a non-aqueous oil phase in the absence of water to provide a mixture; and grinding the mixture.

21 Claims, No Drawings

ANTIPERSPIRANT SUSPENSIONS CONTAINING FINELY DIVIDED ALUMINIUM AND ZIRCONIUM, HAVING BETTER EFFECTIVENESS AND A PROCESS FOR THEIR MANUFACTURE

BACKGROUND OF THE INVENTION

1. Field of the Invention

The subject of the present invention is complexes containing finely-divided aluminium and zirconium in the form of a suspension, which effect particularly good perspiration reduction on human skin, and a process for their synthesis.

2. Description of the Related Art

The prior art already includes a series of patents for the synthesis of aluminium and zirconium complexes that can be used as active ingredients for antiperspirants.

In U.S. Pat. No. 2,814,584 and U.S. Pat. No. 2,814,585 (Daley), for the first time aluminium/zirconium/buffer complexes were described in which urea and glycine act as buffer components. These complexes are also known as ZAG in the case of glycine. Aluminium chlorohydrate (ACH) and $ZrOCl_2$ solutions were taken as the starting point. In U.S. Pat. No. 2,854,382 (Grad), the possibility of using a solution of $ZrO(OH)Cl$ as the Zr source instead of $ZrOCl_2$ is also described. Although a broad range of Al:Zr molar ratios would have been possible, Daley only invokes a ratio of between 1.5:1 and 3.5:1. In the case of Grad, the molar ratio can lie between 0.5:1 and 3.0:1. In U.S. Pat. No. 2,906,688, Beekman et al. describe a further process for the synthesis of stable aluminium/zirconium complexes which is characterised in that it involves heating an aqueous mixture containing $ZrOCl_2 \times 8H_2O$ and aluminium hydroxychloride (ACH) or aluminium trichloride/Al metal. Stable non-gelling solutions with an Al/Zr molar ratio of between 2 and 8 and a pH value of over 3 are obtained.

In their patent GB-2 144 992, Callaghan and Phipps describe the synthesis of active aluminium/zirconium complexes (ZAGs) in which they heated aqueous mixtures containing $ZrO(OH)Cl$, ACH and glycine with an Al/Zr/glycine ratio of 4:1:4 to 50° C., and thus produced a ZAG complex. The composition of such a complex was given by the formula $(Al_2 (OH)_{6-y} X_y)_a (ZrO(OH)_x Cl_{2-x})_b$ neutral amino acid. The designation "activated" is supported by a newly introduced analytical method. This constitutes the usual method in polymer chemistry for determining molecular weight distribution using size-exclusion chromatography. The molecular weight distributions (polymer species distributions) thus determinable differ with the complexes according to Callaghan and Phipps from those in the aforesaid process and indicate, in the eyes of the inventors, the chemical difference of the new complexes.

A series of further patents (U.S. Pat. No. 4,775,528, U.S. Pat. No. 5,114,705, U.S. Pat. No. 5,298,640 and U.S. Pat. No. 5,486,347) were published by Callaghan et al., and include additional process parameters for the heating of the aqueous $ZrO(OH)Cl$, ACH and glycine mixtures, such as the separate heating of the ACH solution to shift the polymer species distribution ("activation") and to dry the reaction solutions.

The concept that the polymer species distribution could be important for effectiveness as an antiperspirant was also applied by Rosenberg et al. to the zirconium components utilised as the product in the patent AU 68983/94. The process described by him is characterised by the following steps:

Firstly, an aqueous mixture of a zirconium salt and glycine is made with a particular polymer species distribution. Next, an activated ACH solution (AACH) is made and reacted with the zirconium solution. This solution was then immediately dried by spray drying.

The table below provides an overview of the ZAG complexes that are registered for the cosmetics industry. The table was issued by the FDA in 1982 as Tentative Final Monograph for Antiperspirant Drug Products for[1].

TABLE 1

Complexes without glycine

| Name | Me/Cl ratio | Al/Zr ratio | Glycine |
|---|---|---|---|
| Aluminium zirconium trichlorohydrate (Al/Zr-3) | 2.1 to 1.5 | 2 to 6 | None |
| Aluminium zirconium tetrachlorohydrate (Al/Zr-4) | 1.5 to 0.9 | 2 to 6 | None |
| Aluminium zirconium pentachlorohydrate (Al/Zr-5) | 2.1 to 1.5 | 6 to 10 | None |
| Aluminium zirconium octachlorohydrate (Al/Zr-8) | 1.5 to 0.9 | 6 to 10 | None |

[1] Translators note: This sentence, the last part of which is already in English in the German patent text, ends as reproduced here.

TABLE 2

Complexes containing glycine as a buffer

| Name | Me/Cl ratio | Al/Zr ratio | Glycine |
|---|---|---|---|
| Aluminium zirconium trichlorohydrex complex (ZAG-3) | 2.1 to 1.5 | 2 to 6 | Variable |
| Aluminium zirconium tetrachlorohydrex complex (ZAG-4) | 1.5 to 0.9 | 2 to 6 | Variable |
| Aluminium zirconium pentachlorohydrex complex (ZAG-5) | 2.1 to 1.5 | 6 to 10 | Variable |
| Aluminium zirconium octachlorohydrex complex (ZAG-8) | 1.5 to 0.9 | 6 to 10 | Variable |

It is known that the aluminium chlorohydrate complexes (ACH) have a polymer structure. These compounds are not particularly effective, i.e. they produce only a slight sweat reduction. They can, however, be altered by heat or chemical additions such that partial depolymerisation of the highly polymerised species takes place. Aluminium chlorohydrate complexes treated in this manner show enhanced effectiveness. It is possible to follow this level of depolymerisation (the "activation" level) with the aid of size-exclusion chromatography (HPLC). According to known teaching, the presence of particular bands in the HPLC spectrum provides information as to whether these compounds have particularly good sweat-reducing properties. In this context, the presence of the so-called Band 3 (or Kd=0.4–0.5) has proved to be particularly important. If Band 3 is large, it was taken that these compounds were particularly effective. In the ensuing period, the ratio of Band 2 to Band 3 was also regarded as an important criterion for assessing effectiveness.

In determining the degree of activation or the sweat reduction capability of Al/Zr compounds, attempts were made to transfer experience gained and methods used in the field of AACH compounds. Al/Zr compounds also show a characteristic band distribution in an HPLC chromatogram. Some researchers have also used Raman and IR spectroscopy to be able to give the bonding details and the effectiveness of these complexes.

Apart from these physical methods, the best means for determining the activation level and effectiveness is the in vitro method—the so-called "hot-room" test, various versions of which are described (A. J. Parisse, in Cosmetic Science and Technology Series, vol. 8, "Clinical Safety and Efficacy Testing of Cosmetics", p. 163–223). Commercially available activated Al/Zr complexes (antiperspirant powders) have better effectiveness than the Zr-free ACH types, although the sweat reduction values achievable are too low for the users' requirements. There was therefore a need for more effective types. There was also a need for stable Al/Zr antiperspirant active agents in a fluid, though not aqueous, form.

In the processing of the known powder-type, activated Al/Zr active agents, problems arose due to the strong tendency of the finely divided powders towards relatively severe dust formation. Therefore, in the further processing of the powder into cosmetic formulations, observing the dust limit values is an important point in preventing any endangering of the health of workers engaged in it.

It has, therefore, not previously been possible to fulfil all the cosmetic industry's requirements with the complexes available.

SUMMARY OF THE INVENTION

Surprisingly, it was discovered that particularly effective aluminium and zirconium-containing antiperspirant agents are obtained if these active ingredients comply with the following formulae and conditions:

$$Al_a(OH)_{(3-b)}X_b (ZrO)_c(OH)_{(2-d)}X_d \text{ (amino acid)}_e$$

where X=a halogen, especially chlorine
and a/c=2.0 to 10.0
(a+c)/(b+d)=0.9 to 2.1
e/c=0 to 2.0
such that at least 60% of the zirconium content can be directly titrated after dissolving in about 0.1 n HCl with EDTA at pH 0.8.

DESCRIPTION OF THE PREFERRED EMBODIMENT

These antiperspirant agents comprise non-aqueous suspensions which are characterised in that the non-aqueous phase consists of a largely unpolarised organic liquid that is not miscible with water, belonging to the substance group alkanes, isoalkanes, monofunctional alcohols, polyfunctional alcohols, fatty acid esters of mono and dibasic carboxylic acids with monofunctional and polyfunctional alcohols, polyoxyethylenes, polyoxypropylenes, polyalkoxylate ethers of alcohols, cyclic silicones, open-chained silicones and combinations of these. In particular, the non-aqueous oil phase consists of silicone oil.

According to the invention, silicone oil components used are cyclic silicones, open-chained silicones or mixtures of these.

The finely divided antiperspirant suspensions according to the invention contain glycine and/or alanine as amino acids.

Analytical determination of the zirconium content in a Zr-containing water-soluble salt is described in the literature in the Fresenius Journal of Analytical Chemistry, Vol. 246, p. 391, 1969, or in US Pharmacopoeia XXIII.

According to this, the Al/Zr complex must be boiled for a long period in strong acid (for digestion). In this way, hydrolysis of the zirconium is reduced, because otherwise, too little zirconium would be found (see also the quote in the Fresenius Journal). It has been found that it is possible, in order to distinguish the active agents according to the invention from the standard complexes, to use a modified analysis process in addition, which differs from the standard procedure outlined above.

This modified procedure is characterised by the following steps:

A small quantity (1 g) of the suspension according to the invention is mixed with 50 ml distilled water in a beaker. The pH value of this mixture is then adjusted to 0.8 with several drops of a 10% salt solution and the solution stirred for 10 minutes. During this time, the Al/Zr compound passes into the aqueous phase and the oil phase separates out.

Next, the EDTA solution is added (20 ml, 0.05 N) and following heating to exactly 50° C., the indicator is added and, before cooling to 40° C., the excess EDTA is titrated back with, for example, an adjusted 0.05 n ZrOCl$_2$ solution (to point of change from yellow to violet or orange to red).

The process for synthesis of finely dispersed antiperspirant suspensions is characterised in that an aluminium salt effective as an antiperspirant is mixed, possibly in the presence of the amino acid, preferably glycine, and with exclusion of moisture in a non-aqueous oil phase, and subsequently ground.

In the process according to the invention, an aluminium salt usable as an antiperspirant is a basic aluminium halide of the following composition:

$$Al(OH)_{(3-b)}X_b$$

where X=halogen, especially chlorine
and b=0.4 to 3, preferably b=0.45 to 1.0

In the presence of an amino acid an aluminium salt effective as an antiperspirant with the following composition is utilised:

$$Al(OH)_{(3-b)}X_b \text{ (amino acid)}$$

where X=halogen, especially chlorine
and b=0.4 to 3, preferably b=0.45 to 1.0
and the molar ratio of the amino acid to aluminium is between 0 and 1.0. Particularly preferred are aluminium complexes of the aforesaid compositions, if during their synthesis an activation step has been passed through.

In the procedure according to the invention, a zirconium salt usable as an antiperspirant is a basic zirconium halide of the following composition:

$$ZrO(OH)_{(2-d)}X_d$$

where X=halogen, especially chlorine
and d=0.5 to 2, preferably d=0.8 to 2

In the presence of the amino acid, e.g. glycine, the formula is as follows:

$$ZrO(OH)_{(2-d)}X_d \text{ (glycine)}$$

where X=halogen, especially chlorine
d=0.5to 2, preferably d=0.8to 2
and the molar ratio of amino acid to Zr is between 0 and 2.0

Grinding of the antiperspirant suspension in the process according to the invention is characterised in that this procedure is carried out at temperatures of below 60° C., particularly below 40° C. The antiperspirant suspensions are advantageously used in cosmetic formulations, for instance in "soft-solids" or "roll-on"s.

The following examples assist in further elucidating the invention:

Examples of Al-Zr-glycine Suspensions

EXAMPLE 1

53.8 kg cyclomethicone (DC 345 from the firm Dow-Corning) is placed in a 150 l reactor with a propeller stirrer. While stirring, the following components are added:

a) 26.68 kg of an activated aluminium chlorohydrate powder with an aluminium content of 26.0% and a chloride content of 17.0% synthesised in accordance with patent U.S. Pat. No. 4,359,456.

b) 20.5 kg of dried $ZrOCl_2$ with a zirconium content of 35.7% and a chlorine content of 27.0%, synthesised by drying commercially available $ZrOCl_2 \cdot 8H_2O$ (from the firm Magnesium Elektron Inc.). Vacuum at 70°–80° C.

c) 6.62 kg glycine

The homogeneous suspension was then finely ground in a ball mill (from the firm Fryma CoBall-Mill) to a final fineness of 99.9%<30 µm and 90%<11 µm. The thixotropic suspension thereby produced is stable with regard to sedimentation. The suspension has a zirconium concentration of 6.82%.

If the zirconium content is determined without prior digestion with concentrated acid by dissolving the aluminium-zirconium-glycinate in about 0.1 n HCl and subsequent titration at pH=0.8 (complexing with 0.05 n EDTA at 50° C./back-titration with 0.05 n $ZrOCl_2$ solution), then a zirconium content of 5.42% is found. This corresponds to 79% of the overall zirconium content.

On the basis of the composition, analysis reveals the molar ratio Al/Zr=3.2 and (Al+Zr)/Cl=1.2, so that according to the FDA nomenclature (FDA-OTC Monograph for Antiperspirants), an aluminium/zirconium-tetrachlorohydrate-glycinate is the result.

EXAMPLE 2

12 kg cyclomethicone (DC 345 from Dow-Corning) is placed in a 50 l reactor with propeller stirrer. While stirring, a powder mixture of the following two components is added:

a) 9.6 kg of an activated aluminium chlorohydrate powder with an aluminium content of 25.7% and a chlorine content of 17.1%, synthesised in accordance with U.S. Pat. No. 4,359,456 and b) 2.4 kg of dried $ZrOCl_2$ with a zirconium content of 35.7% and a chlorine content of 30.4% synthesised by drying commercially available $ZrOCl_2 \cdot 8H_2O$ (from Magnesium Elektron Inc.) in a vacuum at 70°–80° C.

The homogeneous suspension was then ground very finely with a ball mill (from the firm Fryma CoBall-Mill) to a final fineness of 99.9%<30 µm and 95%<10 µm. The thixotropic suspension thereby produced is stable with regard to sedimentation. The suspension has a zirconium content of 4.06%.

If the zirconium content is determined without prior digestion with concentrated acid by dissolving the Al-Zr-chlorohydrate in about 0.1 n HCl and subsequent titration at pH=0.8 (complexing with 0.05 n EDTA at 50° C./back-titration with 0.05 n $ZrOCl_2$ solution), then a zirconium content of 3.08% is found. This corresponds to 76% of the total zirconium content.

On the basis of the composition, analysis reveals the molar ratios Al/Zr=9.7 and (Al+Zr)/Cl=1.51, so that, according to the FDA nomenclature (FDA-OTC Monograph for Antiperspirants), an aluminium/zirconium pentachlorohydrate is the result.

EXAMPLE 3

30.2 g cyclomethicone (DC 345 from Dow Corning) is placed in a laboratory centrifugal ball mill and the following three powder components added:

a) 16.5 g of activated aluminium chlorohydrate powder with an aluminium content of 25.7% and a chlorine content of 17.1%, synthesised in accordance with patent U.S. Pat. No. 4,359,456 and b) 9.6 g of dried ZRO(OH)Cl with a zirconium content of 44.9% and a chlorine content of 19.1%, synthesised by freeze drying a zirconium dichloride oxide solution c) 3.9 g glycine The mixture was then very finely ground to homogenise it with a laboratory centrifugal ball mill to a final fineness of 95%<15 µm. The thixotropic suspension produced thereby is stable with regard to sedimentation. The suspension has a zirconium content of 7.21%.

If the zirconium content is determined without prior digestion with concentrated acid by dissolving the Al/Zr gylcinate in ca. 0.1 n HCl with subsequent titration to pH 0.8 (complexing with 0.05 n EDTA at 50° C./back-titration with 0.05 n $ZrOCl_2$ solution), a zirconium content of 5.03% is found. This corresponds to 70% of the total zirconium content.

On the basis of the composition, analysis reveals molar ratios Al/Zr=3.9 and (Al+Zr)/Cl=1.51, so that according to the FDA nomenclature (FDA-OTC Monograph for Antiperspirants), an aluminium zirconium trichlorohydrate glycinate is the result.

EXAMPLE 4

29.9 g cyclomethicone (DC 345 from Dow Corning) is placed in a laboratory centrifugal ball mill and the 3 following components added as powder:

a) 20.4 g of activated aluminium chlorohydrate powder with an aluminium content of 25.7% and a chlorine content of 17.1%, synthesised according to U.S. Pat. No. 4,359,456 b) 7.2 g of dried $ZrOCl_2$ with a zirconium content of 34.9% and a chlorine content of 27.3%, synthesised by drying commercially available $ZrOCl_2 \cdot 8H_2O$ (from Magnesium Elektron Inc.) in a vacuum at 80° C.

c) 2.52 g glycine.

To homogenise it, the mixture was then very finely ground in a laboratory centrifugal ball mill to a final fineness of 95%<15 µm. The thixotropic suspension created is stable with regard to sedimentation. The suspension has a zirconium content of 4.36%.

If the zirconium content is determined without prior digestion with concentrated acid by dissolving the Al-Zr-glycinate in ca. 0.1 n HCl and subsequent titration at pH=0.8 (complexing with 0.05 n EDTA at 50° C./back-titration with 0.05 n $ZrOCl_2$ solution), a zirconium content of 3.07% is found. This corresponds to 70.4% of the zirconium content.

On the basis of the composition, analysis reveals molar ratios Al/Zr=7.05 and (Al+Zr)/Cl=1.44, so that according to the FDA nomenclature (FDA-OTC Monograph for Antiperspirants), an aluminium/zirconium octachlorohydrate glycinate is the result.

Comparison Example A 30 g cyclomethicone (DC 345 from Dow Corning) is placed in a laboratory centrifugal ball mill and 30 g of a commercially available activated aluminium zirconium tetrachlorohydrate glycinate (available from the firm of Westwood as Westchlor ZR 35B DM) stirred in. To homogenise it, the mixture was then very finely ground with a laboratory centrifugal ball mill to a final fineness of 95%<15 µm. The thin fluid suspension thereby produced is not stable with regard to sedimentation. The suspension has a zirconium content of 5.09%.

If the zirconium content is determined without prior digestion with concentrated acid by dissolving the Al-Zr-glycinate in ca. 0.1 n HCl and subsequent titration at pH=0.8 (complexing with 0.05 n EDTA at 50° C./back-titration with 0.05 n $ZrOCl_2$ solution), a zirconium content of 0.76% is found. This corresponds to 15% of the total zirconium content.

On the basis of the composition, analysis reveals molar ratios Al/Zr=3.54 and (Al+Zr)/Cl=1.07, so that according to the FDA nomenclature (FDA-OTC Monograph for Antiperspirants), an aluminium/zirconium tetrachlorohydrate glycinate is the result.

Comparison Example B

Commercially available aluminium zirconium pentachlorohydrate solution (Zirkonal 50 from the firm of BK Giulini) is dried in a spray tower with an entry temperature of 320° C. and an exit temperature of 105° C. 30 g of the spray dried powder is mixed with 30 g cyclomethicone (DC 345 from Dow Corning).

To homogenise it, the mixture is then very finely ground with a laboratory centrifugal ball mill to a final fineness of 95%<15 µm. The resulting thin fluid suspension is not stable with regard to sedimentation. The suspension has a zirconium content of 4.9%.

If the zirconium content is determined without prior digestion with concentrated acid by dissolving the Al-Zr-chlorohydrate in ca. 0.1 n HCl and subsequent titration at pH=0.8 (complexing with 0.05 n EDTA at 50° C./back-titration with 0.05 n $ZrOCl_2$ solution), a zirconium content of 0.7% is found. This corresponds to 14% of the zirconium content.

On the basis of the composition, analysis reveals molar ratios Al/Zr=7.04 and (Al+Zr)/Cl=1.64, so that according to the FDA nomenclature (FDA-OTC Monograph for Antiperspirants), an aluminium zirconium pentachlorohydrate is the result.

Comparison Example C 30 g cyclomethicone (DC 345, from Dow Corning) is placed in a laboratory centrifugal ball mill and 30 g of a commercially available activated aluminium/zirconium trichlorohydrate glycinate is stirred into it.

To homogenise it, the mixture was then very finely ground in a laboratory centrifugal ball mill to a final fineness of 95%<15 µm. The thin fluid suspension thereby obtained is not stable with regard to sedimentation. The suspension has a zirconium content of 7.40%.

If the zirconium content is determined with prior digestion with concentrated acid by dissolving of the Al-Zr-glycinate in ca. 0.1 n HCl and subsequent titration at pH=0.8 (complexing with 0.05 n EDTA at 50° C./back-titration with 0.05 n $ZrOCl_2$ solution), a zirconium concentration of 1.4% is found. This corresponds to 19% of the total zirconium content.

On the basis of the composition, analysis reveals molar ratios Al/Zr=3.4 and (Al+Zr)/Cl=1.51, so that according to the FDA nomenclature (FDA-OTC Monograph for Antiperspirants), an aluminium zirconium trichlorohydrate glycinate is the result.

Test Method to Determine Efficacy

The most common methods for determining the efficacy of antiperspirants are based on gravimetric determination of the sweat quantity of probands who are subjected to heat stress.

The efficacy of the product according to the invention in Example 1 was tested in comparison with a sample from Comparison Example A and a standard ACH sample at the firm BioSkin Institut für Dermatologische Forschung und Entwicklung GmbH, of Hamburg. The procedure used there uses the proband's back as the test area, where several test fields (5 cm×4 cm) are available. This means that contralateral testing can be carried out with different test samples against a placebo or an untreated field. Using silicone oil (DC345, from Dow Corning), a uniform solid matter concentration of 22% was set for the samples. The products were applied over 3 days in 16 female probands. In order to allow for the semiocclusive conditions in the armpits, after each application of about 3.5 mg/cm$^2$ of the test products, a controlled occlusion of the test fields was undertaken over a period of 150 minutes.

Sweating was evoked on the 4$^{th}$ day by thermal stimulation in a sauna. The sweat was absorbed by occluding adhering cellulose pads and these were then weighed.

Statistical evaluation of the measurement results revealed that the sample according to the invention from Example 1 produces a 22% greater sweat reduction compared with Comparison sample A. Compared with the ACH standard, the Comparison sample A leads to a 25% greater sweat reduction, while the sample according to the invention from Example 1 produces a 53% better sweat reduction.

Subsequently, the suspension according to the invention is incorporated into cosmetic formulations:

The examples given serve to provide an overview of the samples according to the invention in cosmetic formulations and are intended to clarify the invention, and not to restrict it.

Soft solid formulation

| | Components | INCI designation | Proportion by weight (%) |
|---|---|---|---|
| 1 | Sample as Example 3 | Al—Zr-tricholorohydrex Gly | 50 |
| 2 | Gilugel Sil5 | Cyclomethicone pentamer and Al—Mg-hydroxystearate | 10 |
| 3 | DC 345 | Cyclomethicone pentamer | 32 |
| 4 | DC 2-9040 | Cyclomethicone and dimethicone crosspolymer | 5 |
| 5 | DC 200 | Dimethicone | 3 |

Components 2, 4 and 5 are stirred into component 3 and the mixture is homogenised. Component 1 is then stirred in. A thixotropic cream results, in which the oil phase does not separate out during storage.

What is claimed is:

1. An antiperspirant suspension which is finely divided, which is contained in a non-aqueous phase, and which reduces perspiration when used on human skin, comprising:

at least one basic aluminum-zirconium-halogenohydrate complex as active ingredient in which at least 60% of the zirconium content can be directly titrated after dissolving in 0.1 n HCl with EDTA at a pH of 0.8, wherein the active ingredient optionally contains an amino acid.

2. The antiperspirant suspension according to claim 1, wherein the non-aqueous phase consists of an oil.

3. The antiperspirant suspension according to claim 2, wherein the oil of the non-aqueous phase comprises at least one silicone oil selected from the group consisting of cyclical silicones, open-chained silicones, and mixtures thereof.

4. The antiperspirant suspension according to claim 1, wherein the active ingredient contains said amino acid and wherein said amino acid is glycine.

5. The antiperspirant suspension according to claim 1, wherein the at least one basic aluminum-zirconium-halogenohydrate complex is at least one basic aluminum-zirconium chloride.

6. The antiperspirant suspension according to claim 5, wherein the at least one basic aluminum-zirconium chloride has atomic ratios which satisfy conditions as follows:

Al:Zr=2.0 to 10.0 and (Al+Zr):Cl=0.9 to 2.1.

7. The antiperspirant suspension according to claim 1, wherein the active ingredient contains said amino acid and is at least one basic aluminum-zirconium-halogenohydrate-amino acid complex having atomic ratios which satisfy conditions as follows:

Al:Zr=2.0 to 10.0, (Al+Zr):Cl=0.9 to 2.1, and amino acid (glycine): Zr=0.5 to 2.0.

8. A process for the synthesis of an antiperspirant suspension according to the claim 1, comprising:
  a mixing an aluminum salt which is effective as an antiperspirant with a zirconium salt which is effective as an antiperspirant, optionally in the presence of an amino acid, in a non-aqueous oil phase in the absence of water to provide a mixture; and
  b. grinding the mixture.

9. The process according to the claim 8, wherein mixing in step (a) is performed in the presence of the amino acid.

10. The process according to the claim 9, wherein the amino acid is glycine.

11. The process according to the claim 8, wherein the aluminium salt is a basic aluminum chloride having a composition as follows:

$Al(OH)_{(3-x)}Cl_x$, where x=0.4 to 3.

12. The process according to the claim 11, where x=0.45 to 1.0.

13. The process according to the claim 8, wherein mixing in step (a) is performed in the presence of the amino acid which is glycine, wherein the aluminium salt is a basic aluminum chloride having a composition as follows:

$Al(OH)_{(3-x)}Cl_x$, where x=0.4 to 3, and wherein the aluminum salt contains the amino acid glycine.

14. The process according to the claim 13, where x=0.45 to 1.0.

15. The process according to the claim 8, wherein the zirconium salt is a basic zirconium chloride having a composition as follows:

$ZrO(OH)_{(2-y)}Cl_y$, where y=0.5 to 2.

16. The process according to the claim 15, where y=0.9 to 2.

17. The process according to the claim 8, wherein mixing in step (a) is performed in the presence of the amino acid which is glycine, wherein the zirconium salt is a basic zirconium chloride having a composition as follows:

$ZrO(OH)_{(2-y)}Cl_y$, where y=0.5 to 2, and wherein the zirconium salt contains the amino acid glycine.

18. The process according to the claim 17, where y=0.9 to 2.

19. The process according to the claim 8, wherein grinding in step (b) is carried out at temperatures below 50° C.

20. The process according to the claim 19, wherein grinding in step (b) is carried out at temperatures below 30° C.

21. A cosmetic antiperspirant formulation, comprising:
  an antiperspirant suspension according to claim 1, as active ingredient.

* * * * *